(12) United States Patent
Wu et al.

(10) Patent No.: US 11,147,843 B2
(45) Date of Patent: Oct. 19, 2021

(54) **METHOD OF PREVENTING OR TREATING OBESITY USING A NOVEL STRAIN OF *PARABACTEROIDES GOLDSTEINII***

(71) Applicant: Multistars Biotechnology Company Limited, Taoyuan (TW)

(72) Inventors: Po-I Wu, Taoyuan (TW); Chih-Jung Chang, Taoyuan (TW); Yu-Ling Tsai, Taoyuan (TW); Tzu-Lung Lin, Taoyuan (TW)

(73) Assignee: MULTISTARS BIOTECHNOLOGY COMPANY LIMITED, Taoyuan (TW)

( * ) Notice: Subject to any disclaimer, the term of this patent is extended or adjusted under 35 U.S.C. 154(b) by 111 days.

(21) Appl. No.: 16/558,379

(22) Filed: Sep. 3, 2019

(65) Prior Publication Data
US 2020/0078414 A1    Mar. 12, 2020

Related U.S. Application Data (60) Provisional application No. 62/726,469, filed on Sep. 4, 2018.

(51) Int. Cl.
*A61K 39/00* (2006.01)
*A61K 39/02* (2006.01)
*A61K 45/00* (2006.01)
*A61K 35/74* (2015.01)
*A61P 3/04* (2006.01)
*A61K 9/00* (2006.01)

(52) U.S. Cl.
CPC ............ *A61K 35/74* (2013.01); *A61P 3/04* (2018.01); *A61K 9/0053* (2013.01)

(58) Field of Classification Search
CPC ......... A61K 39/00; A61K 39/02; A61K 45/00
USPC .................... 424/93.1, 93.4, 234.1, 278.1
See application file for complete search history.

*Primary Examiner* — Rodney P Swartz
(74) *Attorney, Agent, or Firm* — WPAT, PC (57) ABSTRACT

The present invention provides a method of preventing or treating obesity by administering the probiotic bacterium of a novel *Parabacteroides goldsteinii* strain to the subject in need. The novel *Parabacteroides goldsteinii* strain is derived from the gastrointestinal tract of an individual and has better aero-tolerance and better acid-tolerance therefore it has better environmental tolerance to adapt to different living environments. The novel *Parabacteroides goldsteinii* strain not only can effectively prevent the weight gain of the individual, but also can effectively slow down the weight gain of the obese individual; therefore, the novel *Parabacteroides goldsteinii* strain of the present invention can be used for preparing a pharmaceutical composition for prevention and/or treating obesity.

13 Claims, 10 Drawing Sheets

METHOD OF PREVENTING OR TREATING OBESITY USING A NOVEL STRAIN OF *PARABACTEROIDES GOLDSTEINII*

CROSS-REFERENCE TO RELATED APPLICATION

This application claims priority of U.S. provisional application No. 62/726,469, filed on Sep. 4, 2018, the content of which are incorporated herein in its entirety by reference.

BACKGROUND OF THE INVENTION

1. Field of the Invention

The present invention relates to a method of using a novel strain of *Parabacteroides goldsteinii*, and more particularly to a method of using the novel strain of *Parabacteroides goldsteinii* for preventing or treating obesity, wherein the novel strain of *Parabacteroides goldsteinii* is DSM 32939.

2. The Prior Art

In recent years, the incidence of obesity in the world has gradually increased. The World Health Organization (WHO) described the rapid spread of obesity as an "infectious disease" and called it "Globesity." According to estimates by the World Health Organization in 2014, about 39% of the population around the world is overweight (about 1.9 billion people), and 13% of the population is obese (about 600 million people). With the changes in eating habits and the improvement of life quality, the prevalence of obesity in Taiwan has also increased year by year. According to the national nutrition and health status survey released by the National Administration, Ministry of Health and Welfare, the prevalence rate of overweight or obesity in adults is as high as 43%, while the ratio of male and female is 49% and 40% respectively. In other words, one in every two males in Taiwan is overweight or obese, and one in every two to three women is overweight or obese, and more than 200,000 of them have reached the standard of morbid obesity, and must be treated with surgery.

Obesity increases the risk of multiple health problems and may lead to a variety of complications in individuals, including hypertension, hyperlipidemia, cardiovascular disease, sleep apnea, angina, degenerative arthritis, uric acid excessive osteoarthritis, type 2 diabetes, and cancer. Therefore, obesity would reduce the quality of life and may lead to premature death, so the average life expectancy of morbidly obese patients is much less than that of normal weight. Although genes may be involved in the development of obesity, obesity epidemics are mainly attributed to high-calorie diets and sedentary lifestyles. Therefore, changes in lifestyle can prevent obesity and complications thereof.

While low-calorie diets and regular exercise can be used to reduce weight and treat obesity, these methods are difficult to implement and their efficacy is limited, primarily because of the adaptive physiological mechanisms that maintain energy storage in the body. In addition, some drugs have been approved for long-term obesity treatment such as orlistat, phentermine, or topiramate; however, these drugs often cause serious side effects, thus limiting the efficacy of treatment and patient compliance. Furthermore, bariatric surgery can significantly reduce the body weight, but this type of interventional surgery is not suitable for all overweight people; for these reasons, it is indeed necessary to study safe and effective ways to reduce body weight and fat accumulation.

Therefore, in summary, it is necessary to find a new strain of *Parabacteroides goldsteinii* which is derived from the gastrointestinal tract and can be well adapted to the gastrointestinal environment, and at the same time can effectively achieve the slimming effects.

SUMMARY OF THE INVENTION

An objective of the present invention is to provide a method of using a novel strain of *Parabacteroides goldsteinii*, the metabolite thereof, or the bacterial component thereof for modulating the physiology of a subject in need thereof to inhibit or treat obesity.

To solve the foregoing problem, the present invention provides a method of preventing or treating obesity, comprising administering to a subject in need thereof a composition comprising an effective amount of the *Parabacteroides goldsteinii* (hereinafter referred to as *P. goldsteinii*) strain MTS01, a metabolite thereof, or the bacterial component thereof; wherein the *P. goldsteinii* strain MTS01 is DSM32939.

According to an embodiment of the present invention, the novel strain of *Parabacteroides goldsteinii* enhances its own environmental tolerance to be better adapted to different living environments, especially the gastrointestinal tract of individuals with strong acid environment; wherein the environmental tolerance is aero-tolerance or acid-tolerance.

According to an embodiment of the present invention, the composition effectively directly inhibits the body weight gain of a normal (i.e. non-obese) individual to effectively prevent obesity in an individual; at the same time, the composition can effectively inhibit the body weight gain of an obese individual to effectively achieving the effect of treating obesity.

According to an embodiment of the present invention, the *P. goldsteinii* is a live bacterium; and the composition further comprises bacteria other than *P. goldsteinii*.

According to an embodiment of the present invention, the effective amount of the *P. goldsteinii* is at least $2 \times 10^9$ CFUs/kg of body weight per day, and the administration period may be around 8-16 weeks.

The use of the *Parabacteroides goldsteinii* of the present invention in the prevention or treatment of obesity can be, but is not limited to, oral administration to the subject in need thereof. The composition can be orally administered along with food; therefore, the preparation of the composition comprising the *Parabacteroides goldsteinii* of the present invention can further include a protein, a monosaccharide, a disaccharide, an oligosaccharide, an oligosaccharide, a polysaccharide, a carbohydrate, an amino acid, a lipid, a vitamin, or any combination well-known in the art.

Otherwise, the preparation of the composition comprising the *Parabacteroides goldsteinii* strain MTS01 of the present invention can further include a pharmaceutically acceptable excipient, carrier, adjuvant, or food additive. The composition is in the form of, but is not limited to, a solution, a gelatin capsule, a soft capsule, or a tablet in order to transfer the *Parabacteroides goldsteinii* of the present invention to the intestinal tract or to partially or fully colonize the intestinal tract. Simultaneously, the *Parabacteroides goldsteinii* of the present invention or the composition containing other ingredients can further use in the preparation of a food, a health food, or a dietary supplement.

Previous studies have found that in mice fed with high fat diet, the oral administration of the *Parabacteroides goldsteinii* strain JCM13446 can significantly reduce the obesity situation in individuals. However, the strain JCM13446 is purchased from the American Type Culture Collection (ATCC) with the number ATCC BAA-1180 and is a clinical isolate cultured from abdominal fluid of human intestinal origin. The strain JCM13446 is not directly isolated from the gastrointestinal tract of an individual; therefore, the strain may have doubts that are not practically well adapted to the gastrointestinal environment of individuals, and may also substantially reduce its utility in practical applications as an oral probiotic. For example, the amount of bacteria actually colonizing the gastrointestinal flora is lower than the expected one due to the inability to pass the strong acid or alkali environment in the stomach and intestines.

The results of the whole-genome analysis indicate that there are 5,498 predicted protein-coding genes in the novel *Parabacteroides goldsteinii* strain MTS01 isolated from the feces of C57BL/6 mice. Wherein, compared with the *Parabacteroides goldsteinii* strain JCM13446, which is a clinical isolate cultured from abdominal fluid of human intestinal origin, the 586 genes of these 5,498 genes of the strain MTS01 are only 70% or less identical to the strains JCM13446, and the 610 genes of the *Parabacteroides goldsteinii* strain MTS01 of the present invention are not present in the strain JCM13446, indicating that the *Parabacteroides goldsteinii* strain MTS01 of the present invention and the strain JCM13446 have a high degree of genomic variability, and the 610 unique genes in the strain MTS01 of the present invention may get via horizontal gene transfer, where these genetic determinants may be obtained from other commensal bacteria through bacterium-bacterium genetic determinants transfer machinery.

Moreover, the results of the protein annotation analysis indicate that the number of genes encoding phages, prophages, transposable elements, and plasmids of the strain MTS01 is significantly higher than that of the strain JCM13446. Based on the results, the species of the polysaccharide-related gene among the *Parabacteroides goldsteinii* strain MTS01 of the present invention and the strain JCM13446 are further analyzed, and the results show that the number of genes associated with polysaccharides, monosaccharides, di-saccharides, oligo-saccharides, central carbohydrate metabolism and amino-sugars is all higher in strain MTS01 than in strain JCM13446, and the number of glycosyltransferases in the *Parabacteroides goldsteinii* strain MTS01 of the present invention is significantly higher than that in strain JCM13446. The results indicate that the *Parabacteroides goldsteinii* strain MTS01 of the present invention has more abilities on polysaccharides utilization and gains more genes for growth fitness, which enables the strain MTS01 of the present invention to better adapt to the environment of the individual gastrointestinal tract.

The environmental tolerance of these two strains is further performed, and the results show that the *Parabacteroides goldsteinii* strain MTS01 of the present invention has better aero-tolerance and better acid-resistance than the strain JCM13446, and can be better adapted to different living environments, especially the gastrointestinal tract of individuals with strong acid environment.

Finally, results of the effect on preventing obesity indicate that the *Parabacteroides goldsteinii* strain MTS01 of the present invention can more significantly inhibit the body weight gain of individuals fed a high-fat diet and more effectively reduce the body weight change rate compared to the strain JCM13446, and the *Parabacteroides goldsteinii* strain MTS01 of the present invention can also significantly inhibit the subcutaneous fat mass gain of individuals fed the high-fat diet, indicating that the *Parabacteroides goldsteinii* strain MTS01 of the present invention has better effect on preventing the obesity and can more effectively inhibit the obesity of individuals than the strain JCM13446, and achieve the effect of inhibiting obesity. At the same time, the results of the effect on inhibiting the body weight gain of obese individuals indicate that the *Parabacteroides goldsteinii* strain MTS01 of the present invention can not only effectively prevent the obesity of an individual, but also effectively slow down the body weight gain of an obese individual to achieve the effect of treating obesity.

The present invention provides a novel *Parabacteroides goldsteinii* strain MTS01 for the preparation of a pharmaceutical composition for preventing or treating obesity; wherein the *Parabacteroides goldsteinii* strain MTS01 of the present invention is derived from the gastrointestinal tract and is a probiotic strain which can well adapt to the gastrointestinal environment that can enhance the benefits of the probiotic strain in practical application, and the probiotic strain has simultaneously more effectively effects of preventing and treating obesity; therefore, the *Parabacteroides goldsteinii* strain MTS01 of the present invention can be effectively applied to the prevention or treatment of obesity and the preparation of related pharmaceutical compositions.

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

DETAILED DESCRIPTION OF THE PREFERRED EMBODIMENT

Statistical analysis is performed using Excel software. Data are expressed as mean±standard deviation (SD), and differences between groups are statistically analyzed by one-way ANOVA.

The data provides in the present invention represent approximated, experimental values that vary within a range of ±20%, preferably ±10%, and most preferably ±5%.

Definition

The "effective amount" described herein is the amount of the needed amount of the *Parabacteroides goldsteinii* strain MTS01 of the present invention that can directly inhibit the body weight gain of a mammal or a human, or inhibit the body weight gain of an obesity mammal or an obesity human. The effective amount varies depending on the species or individual being treated, but the effective amount can be determined experimentally by, for example, a dose escalation test.

According to the present invention, the operating procedures and parameter conditions for bacterial culture are within the professional literacy and routine techniques of those having ordinary skill in the art.

The "metabolite" described herein is a substance which is secreted into the bacterial culture solution after being metabolized by the bacteria, comprising the culture medium for culturing the bacteria.

The "the bacterial component thereof" described herein is a derivative substance directly or indirectly related to the bacterium when it is cultured, including but not limited to the metabolic product of the bacterium, the structure of the bacterium, the bacteria-related activity and the inactive ingredient, etc.

The present invention provides a method of a strain of *Parabacteroides goldsteinii* strain MTS01 for the preparation of a pharmaceutical composition for preventing or treating obesity. The following results of whole-genome analysis show that the *Parabacteroides goldsteinii* strain MTS01 of the present invention has a high degree of genomic variability compared to the commercial *Parabacteroides goldsteinii* strain JCM13446; and the results of protein annotation analysis of the whole-genome show that the *Parabacteroides goldsteinii* strain MTS01 of the present invention has more abilities on polysaccharides utilization and gains more genes for growth fitness, which enables the strain MTS01 of the present invention to better adapt to the environment of the individual gastrointestinal tract. Furthermore, the results of the in vitro experiments in cells showed that the *Parabacteroides goldsteinii* strain MTS01 of the present invention has better aero-tolerance and acid tolerance than the JCM13446 strain, so that the strain MTS01 of the present invention has better environmental tolerance. The results of the in vivo experiments in animals show that, compared with the JCM13446 strain, the *Parabacteroides goldsteinii* strain MTS01 of the present invention has better anti-obesity effect, can effectively inhibit the obesity of an individual, and achieve the effect of inhibiting obesity. The *Parabacteroides goldsteinii* strain MTS01 of the present invention can not only effectively prevent obesity in an individual, but also effectively slow down the body weight gain of obese individuals to achieve the effect of treating obesity. In general, an effective dose of a mammal or a human of the present invention of the *Parabacteroides goldsteinii* is at least $2 \times 10^9$ CFUs/kg, as described in detail below.

The Strain of the *Parabacteroides goldsteinii* of the Present Invention

The novel *Parabacteroides goldsteinii* (*P. goldsteinii*) strain MTS01 used in the examples of the present invention for preventing or treating obesity is isolated from the feces of C57BL/6 mice and is deposited in Deutsche Sammlung von Mikroorganismen und Zellkulturen (DSMZ; Inhoffenstr. 7B, D-38124 Braunschweig, Germany) on Oct. 29, 2018, and the number is DSM 32939. *P. goldsteinii* is an obligate anaerobe that needs to be cultured in an anaerobic incubator at 37° C. for about 48 hours, wherein the culturing system contains 10% $CO_2$, 10% $H_2$, and 80% $N_2$. The liquid culture medium of the *P. goldsteinii* is NIH thioglycollate broth (TGC II) (purchased from BD, USA, No. 225710), and the solid culture medium is Anaerobic blood agar plate (Ana. BAP) (purchased from CREATIVE LIFESCIENCES, Taiwan). The *P. goldsteinii* is stored in a −80° C. refrigerator for a long-term preservation, and the protective liquid is 25% glycerin. It does not need special cooling treatment and can be stored by freeze drying to stabilize its activity.

In the examples of the present invention, the conventional strain of commercial *Parabacteroides goldsteinii* JCM13446 is used as control to analyze and compare the characteristics and microbiological properties of the novel strain of *Parabacteroides goldsteinii* MTS01 of the present invention.

As the results of the whole-genome analysis, in the 5,498 genes, which encode proteins, of the strain MTS01 of the present invention, there are 586 genes with only sequence identity of 70% or less when compared with the strain JCM13446 isolated from abdominal fluid of human intestinal origin. Besides, the 610 genes of the strain MTS01 cannot find in the strain JCM13446, indicating that compared with the conventional strain of *Parabacteroides goldsteinii*, the strain MTS01 of the present invention has a high degree of genomic variability. As the results of protein annotation analysis of the whole-genome, the number of genes associated with phages, prophages, transposable elements, plasmids, polysaccharides, monosaccharides, di-saccharides, oligo-saccharides, central carbohydrate metabolism and amino-sugars is all higher in strain MTS01 than in strain JCM13446. In addition, the number of glycosyltransferases in strain MTS01 is higher than those in strain JCM13446. These results imply that compared with the conventional *Parabacteroides goldsteinii* strain, the strain MTS01 of the present invention has more abilities on polysaccharides utilization and gains more genes for growth fitness, which enables the strain MTS01 of the present invention to better adapt to the environment of the individual gastrointestinal tract.

Meanwhile, from the results of the in vitro experiments in cells, the *Parabacteroides goldsteinii* strain MTS01 of the present invention has better aero-tolerance and acid tolerance than the JCM13446 strain, so that the strain MTS01 of the present invention has better environmental tolerance, and can be better adapted to different living environments, especially the gastrointestinal tract of individuals with a strong acid environment. From the results of the in vivo experiments in animals, compared with the JCM13446 strain, the *Parabacteroides goldsteinii* strain MTS01 of the present invention can significantly inhibit more the body weight gain, reduce more the body weight changes, and reduce more subcutaneous fat mass gain of individuals fed with a high-fat diet, indicating that the strain MTS01 of the present invention has better anti-obesity effect than the conventional *Parabacteroides goldsteinii* strain. The strain MTS01 of the present invention cannot only effectively prevent obesity in an individual, but also effectively slow down the body weight gain of obese individuals to achieve the effect of treating obesity, indicating that the *Parabacteroides goldsteinii* strain MTS01 of the present invention can be effectively used for the preparation of a pharmaceutical composition of preventing or treating obesity.

The "probiotic or probiotic bacteria" described herein is a microorganism the cells thereof, the mixed strains, the extracts or the metabolites with a positive effect on the host itself, usually derived from the human body and beneficial to intestinal health. Probiotic or probiotic bacteria can also refer to certain microorganisms that are externally supplemented and are beneficial to the body. Wherein, the metabolite of the probiotic or probiotic bacteria is a substance which is secreted into the bacterial culture solution after being metabolized by the bacteria, comprising the culture medium for culturing the bacteria.

According to the present invention, the operating procedures and parameter conditions for bacterial culture are within the professional literacy and routine techniques of those having ordinary skill in the art.

Experimental Mice

In the present invention, four-week-old, specific pathogen-free, C57BL/6J male mice were purchased from National Applied Research Laboratories, NARLab, Taiwan. All mice were fed ad libitum with chow and water. Animals were housed four to five individuals per cage with free access to food and sterile drinking water (DW) (reverse osmosis grade) in a temperature-controlled room (19-23° C.) under a 12 hours dark-light cycle. Animals were housed in a specific pathogen-free facility and were treated in accordance with guidelines from the National Institutes of Health (USA). At the time indicated, non-fasting animals were anaesthetized and whole blood was withdrawn by cardiac puncture. Visceral adipose tissues (i.e., epididymal white adipose tissues) and the liver were removed and weighed. Organs and tissues were immersed in liquid nitrogen and stored at −80° C. for further analysis.

Example 1

Whole-Genome Comparison of the *Parabacteroides goldsteinii* Strain MTS01 with the Strain JCM13446

In the embodiment of the present invention was to compare the whole-genome differences and identity between the *Parabacteroides goldsteinii* strain MTS01 of the present invention and the strain JCM13446, wherein the genome sequence of the *Parabacteroides goldsteinii* strain JCM13446 has been preserved in GenBank. (RefSeq assembly: GCF_000969835.1), and the *Parabacteroides goldsteinii* strain JCM13446 has 7 contigs in the whole genome, and has a total of 6,486,757 nucleotide pairs (bps) in the whole genome.

In order to perform the de novo sequencing of the *Parabacteroides goldsteinii* strain MTS01 of the present invention, the sequencing platform of Illumina and Pacbio was first used to perform the next generation Sequencing (NGS), and then obtained reads of several gene sequences, followed by hybridization-assembly to construct the whole genome of the strain MTS01. The main steps were as follows: First, the sequence reads obtained from the Pacbio sequencing platform were first assembled by Canu, and then the contigs were mapped by Pacbio reads using Minimap2 and corrected the assembled results by Racon; for example, reversing the inverted contigs or separating the incorrectly assembled contigs. Then, short reads were mapped to the assembled contigs by BWA and Pilon was carried out to correct the sequences.

Among them, Canu is a branch of Celera Assembler, designed specifically for the assembly of high-noise single-molecule sequencing reads obtained by PacBio and other sequencing platforms, and Celera Assembler is a DNA sequence assembler for de novo whole-genome shotgun (WGS); and Minimap2 is a universal alignment program for DNA sequences or long mRNA sequences with large reference databases. For comparison, the sequence alignment method of Minimap2 is performed by split-read alignment, which uses a concave gap to insert and delete long-sequence reads, and introducing new heuristics to reduce spurious alignments; BWA is a program that plots low-divergent sequences for larger reference genomes (such as the human genome); Pilon is a program used to compare the inconsistencies between the entered genome and the reads, and is often used to manually correct the whole-genome sequence to be analyzed.

Next, the result of the whole-genome sequencing analysis of the *Parabacteroides goldsteinii* strain MTS01 of the present invention was used to predict the open reading frame by MetaGeneMark (i.e. predicting whether the whole-genome sequence contains genes encoding proteins). The predicted genes will be annotated separately through three data databases: KEGG, COG, and NCBI-NR; wherein, Blast (Basic Local Alignment Search Tool, which is used to compare the primary structure of biological sequences, such as the amino acid sequence of different proteins or the DNA sequence of different genes, is primarily compared to information in a database known to contain several sequences, and BLAST is used to find existing sequences that are identical or similar to the sequence to be analyzed, in order to predict its efficacy or role, etc.) was searched in the data database of KEGG and NCBI-NR; and the search of COG data database was completed through the CD search (Conserved Domain Search Service), wherein the data databases were built in the software. Finally, a circular genome plot of the *Parabacteroides goldsteinii* strain MTS01 of the present invention was prepared using Circos, and the results were shown in FIG. 1; wherein, Circos is software for visualizing data and information that visualizes the resulting genomic data and information in a circular fashion.

After obtaining the whole-genome sequencing and gene sequence analysis of the *Parabacteroides goldsteinii* strain MTS01 of the present invention, the BLASTP (Protein BLAST) was used to compare and analyze the identity of amino acid level and protein level between *Parabacteroides goldsteinii* strain MTS01 of the present invention and strain JCM13446; wherein, when BLASTP was performed, the set value of –evalue was $1^{-10}$, the set value of –max_target_seqs was 1, and the set value of –outfmt was 6. Next, The R Foundation was used to plot the histogram of the identity distribution of the amino acid of the *Parabacteroides goldsteinii* strain MTS01 and the strain JCM13446, and the result were shown in FIG. 2A. Then, Circos was used to prepare a distribution map of the cyclic amino acid identity in genomes of these two strains, and the results were shown in FIG. 2B.

Figure 1:
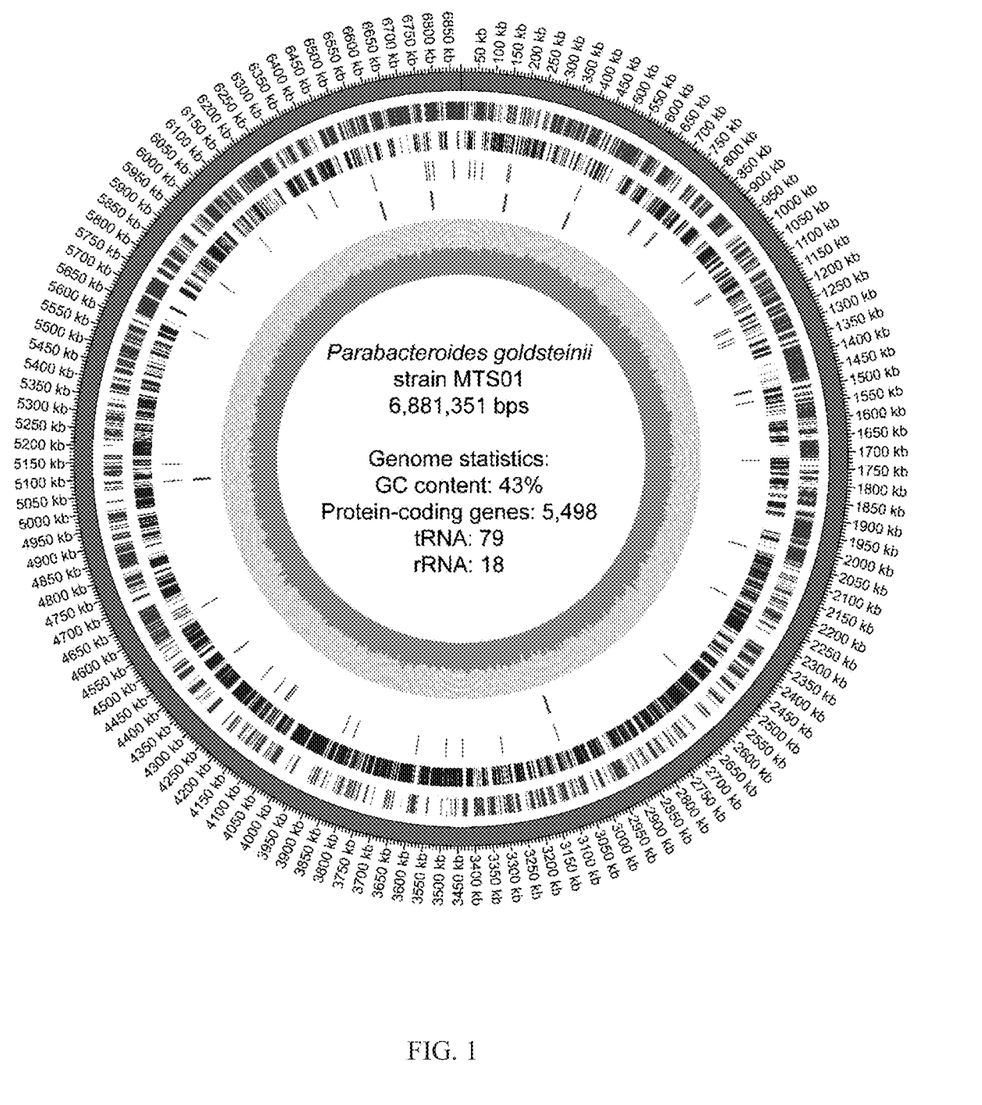
FIG. 1 shows that the circular genome map of the whole-genome sequence analysis of the *P. goldsteinii* strain MTS01.

The circular genome map of the whole-genome sequence analysis of the *Parabacteroides goldsteinii* strain MTS01 of the present invention was shown in FIG. 1; wherein the first circle from the outer side to the inner side represented the position of the genome, and the second circle represented the predicted gene on the direct strand, the third circle represented the predicted gene on the complementary strand, the fourth circle represented the position of the tRNA, the fifth circle represented the position of the rRNA, and the innermost circle represented the GC content of the whole-genome of the strain MTS01. As shown in FIG. 1, the total length of the whole-genome sequence of the *Parabacteroides goldsteinii* strain MTS01 of the present invention through the sequencing platform of Illumina and Pacbio was 6,881,351 base pairs and the results of the annotation of the genome shows that there were 5,498 predicted protein-coding genes in the *Parabacteroides goldsteinii* strain MTS01 of the present invention.

Figure 2A:
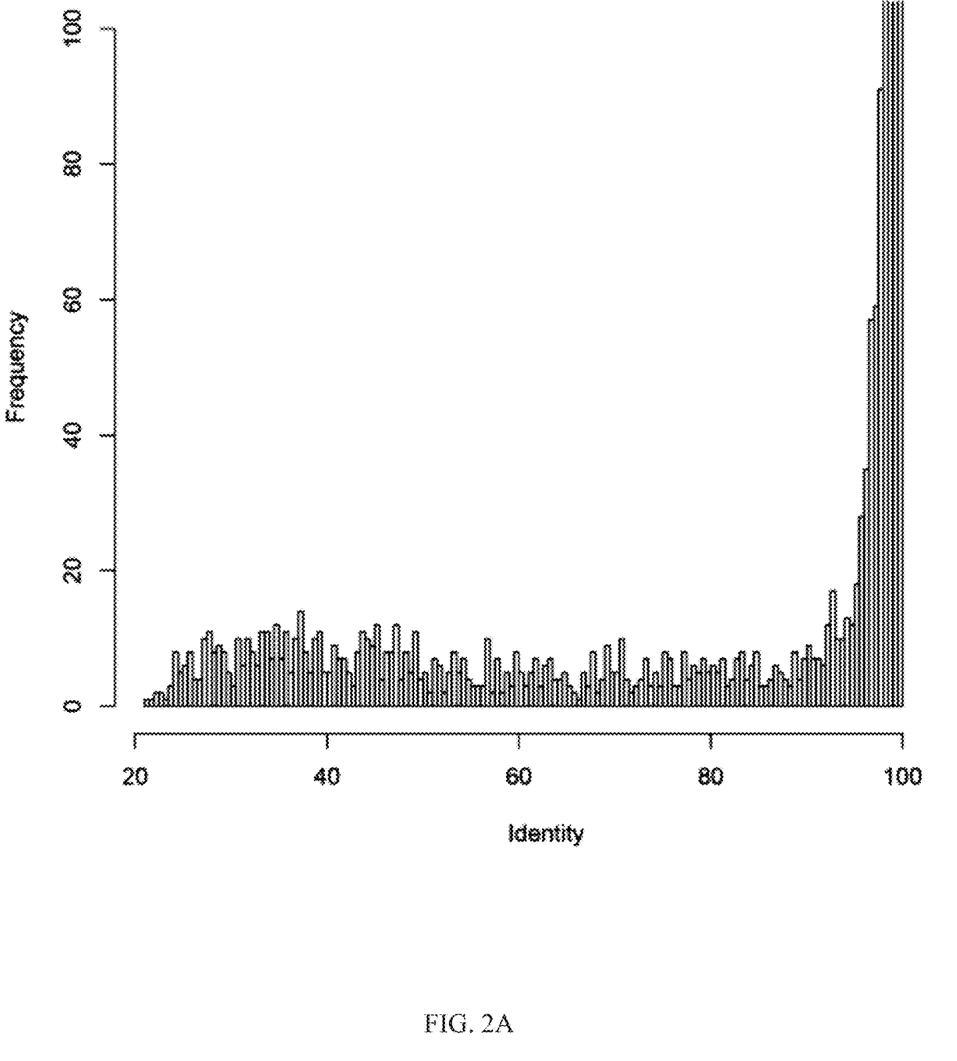
FIG. 2A shows that the identity from the protein annotation analysis of the whole-genome between the *P. goldsteinii* strain MTS01 and the strain JCM13446.
Figure 2B:
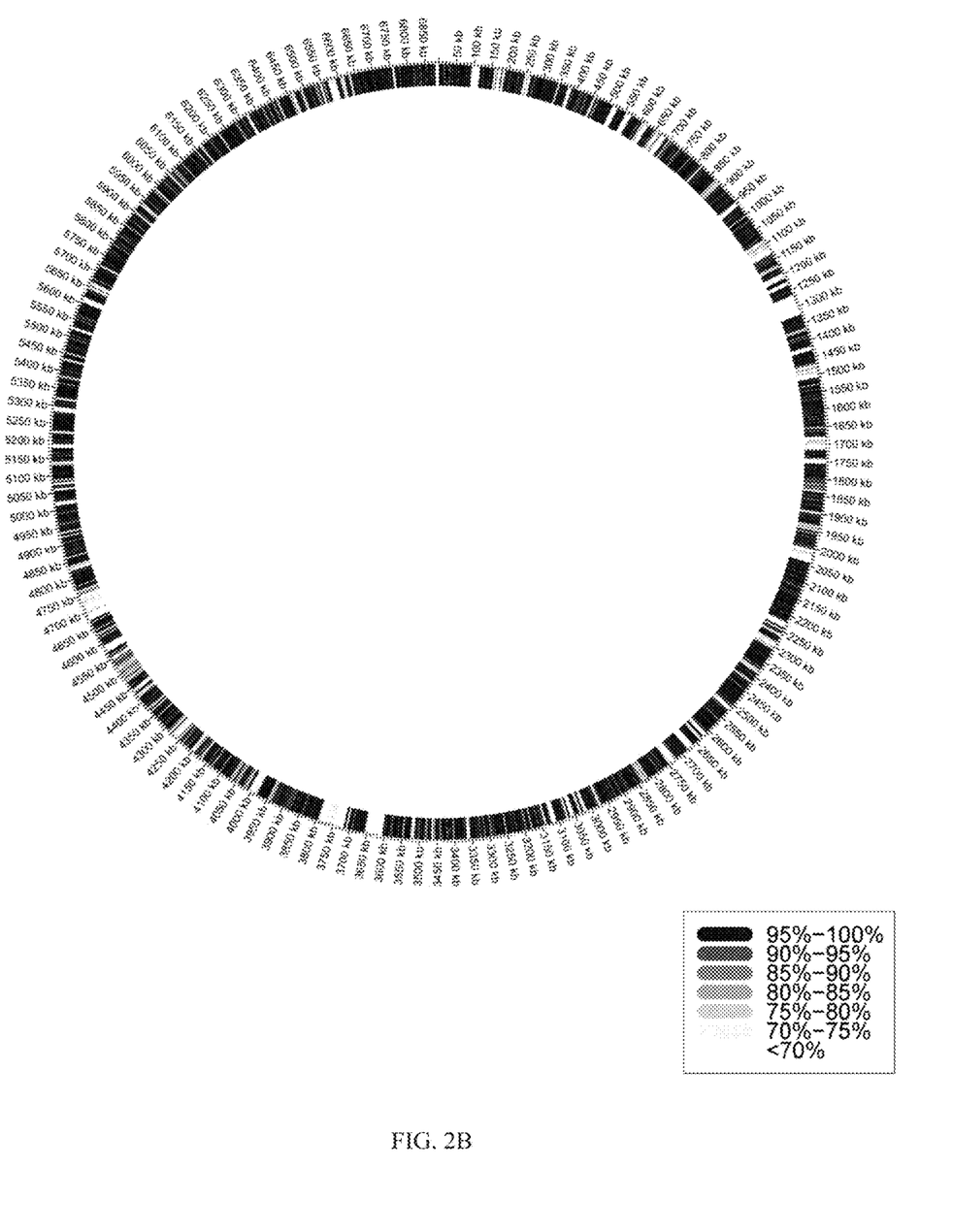
FIG. 2B shows that full-view of the whole-genome distribution of the cyclic amino-acid identity between the *P. goldsteinii* strain MTS01 and the strain JCM13446.

The results of protein annotation analysis of the whole-genome of the *Parabacteroides goldsteinii* strain MTS01 of the present invention and the strain JCM13446 were shown in FIG. 2A; the full-view of the whole-genome distribution of the cyclic amino-acid identity and similarity between the strain MTS01 and the strain JCM13446, which were based on the chromosomal organization of strain MTS01 and the comparison with the JCM13446 strain, were shown in FIG. 2B; wherein, the color represented the score of the identity (%), including several clusters with low identity (lighter gray).

As showing in FIG. 2A, based on the comparison results of the protein annotation analysis, among the 5,498 protein-coding genes of the *Parabacteroides goldsteinii* strain MTS01 of the present invention, 586 genes were only 70% or less identical to the strain JCM13446, and the 610 genes of the *Parabacteroides goldsteinii* strain MTS01 of the present invention could not find a corresponding gene in the strain JCM13446, indicating that the 610 genes were unique in the strain MTS01 of the present invention. As showing in FIG. 2B, the distribution of each gene in the whole-genome between these two strains were observed, wherein the genes with lower identity between the strain MTS01 of the present invention and the strain JCM13446, and the aforementioned 610 genes, that were not present in the strain JCM13446, were clustered together in the whole-genome, suggesting that these genes, which were only present in the strain MTS01 of the present invention, may be obtained from other commensal bacteria through bacterium-bacterium genetic determinants transfer machinery. The results of the above whole-genome analysis revealed that the *Parabacteroides goldsteinii* strain MTS01 of the present invention and the strain JCM13446 had a high degree of genomic variability.

Example 2

Protein Annotation Comparison of the *Parabacteroides goldsteinii* Strain MTS01 with the Strain JCM13446

In the embodiment of the present invention was to compare the protein annotation differences and identity between the *Parabacteroides goldsteinii* strain MTS01 of the present invention and the strain JCM13446. First, RAST (Rapid Annotation using Subsystem Technology) server was used to generate a SEED protein family annotation, and the results were shown in FIG. 3A; wherein, RAST is a fully automated service for annotating complete or nearly complete bacterial and archaeal genomes to provide consistent and accurate genomic annotation in thousands of genomes, providing high quality genomic annotations for these genomes throughout the lineage development tree.

Figure 3A:
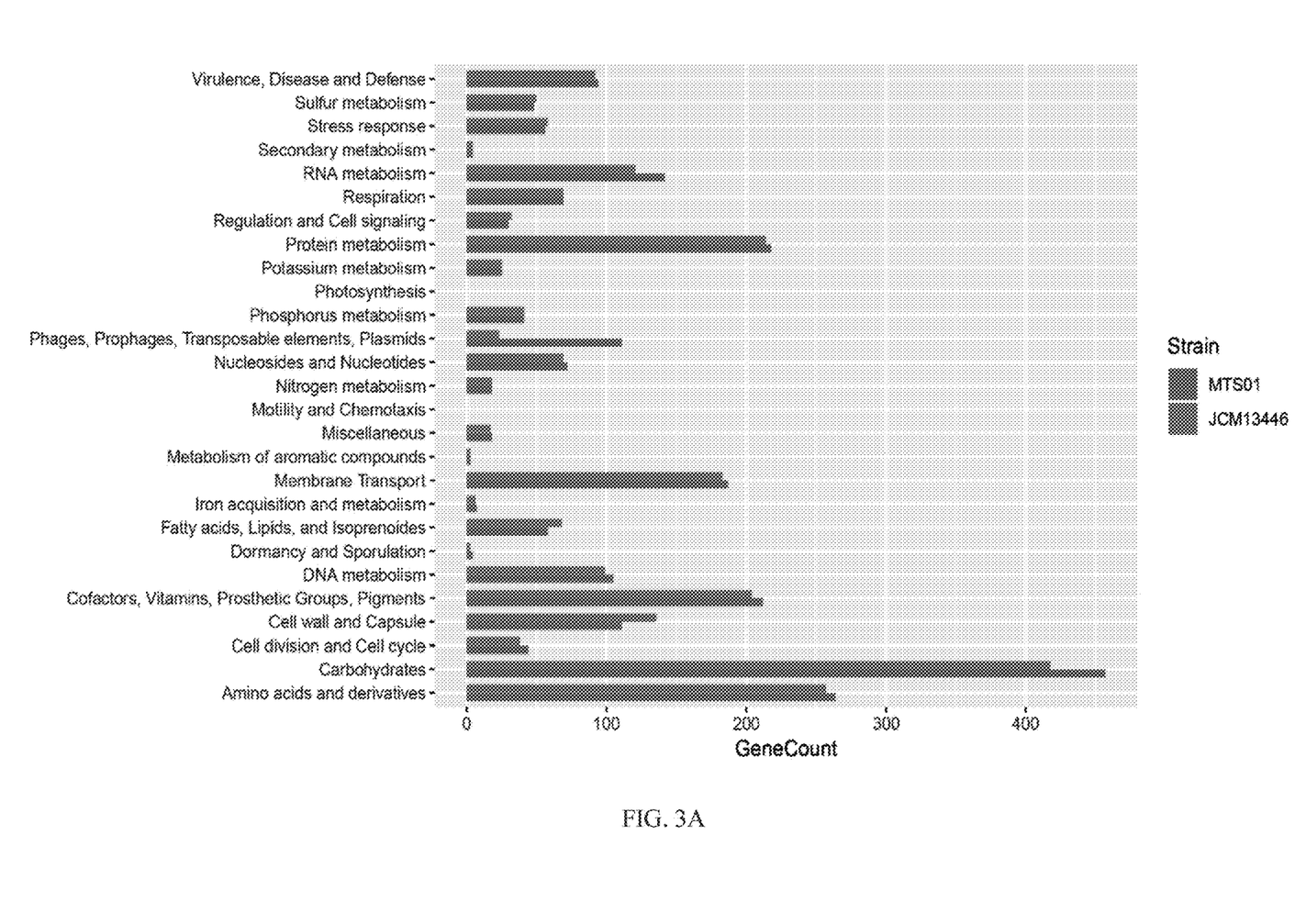
FIG. 3A shows that the functional annotations of the whole gene between the *P. goldsteinii* strain MTS01 and the strain JCM13446.

The function of SEED protein family annotation was used to analyze the functional annotations of the whole gene of the *Parabacteroides goldsteinii* strain MTS01 of the present invention and the strain JCM13446 and the results were shown in FIG. 3A. From the results of Example 1, the unique gene cluster in the *Parabacteroides goldsteinii* strain MTS01 of the present invention may be obtained by horizontal gene transfer, and as showing in FIG. 3A, the number of genes encoding phages, prophages, transposable elements, and plasmids of the strain MTS01 was significantly higher than that of the strain JCM13446; moreover, in the *Parabacteroides goldsteinii* strain MTS01 of the present invention the genes encoding polysaccharides synthesis and polysaccharides utilization were also more than of the strain JCM13446.

Figure 3B:
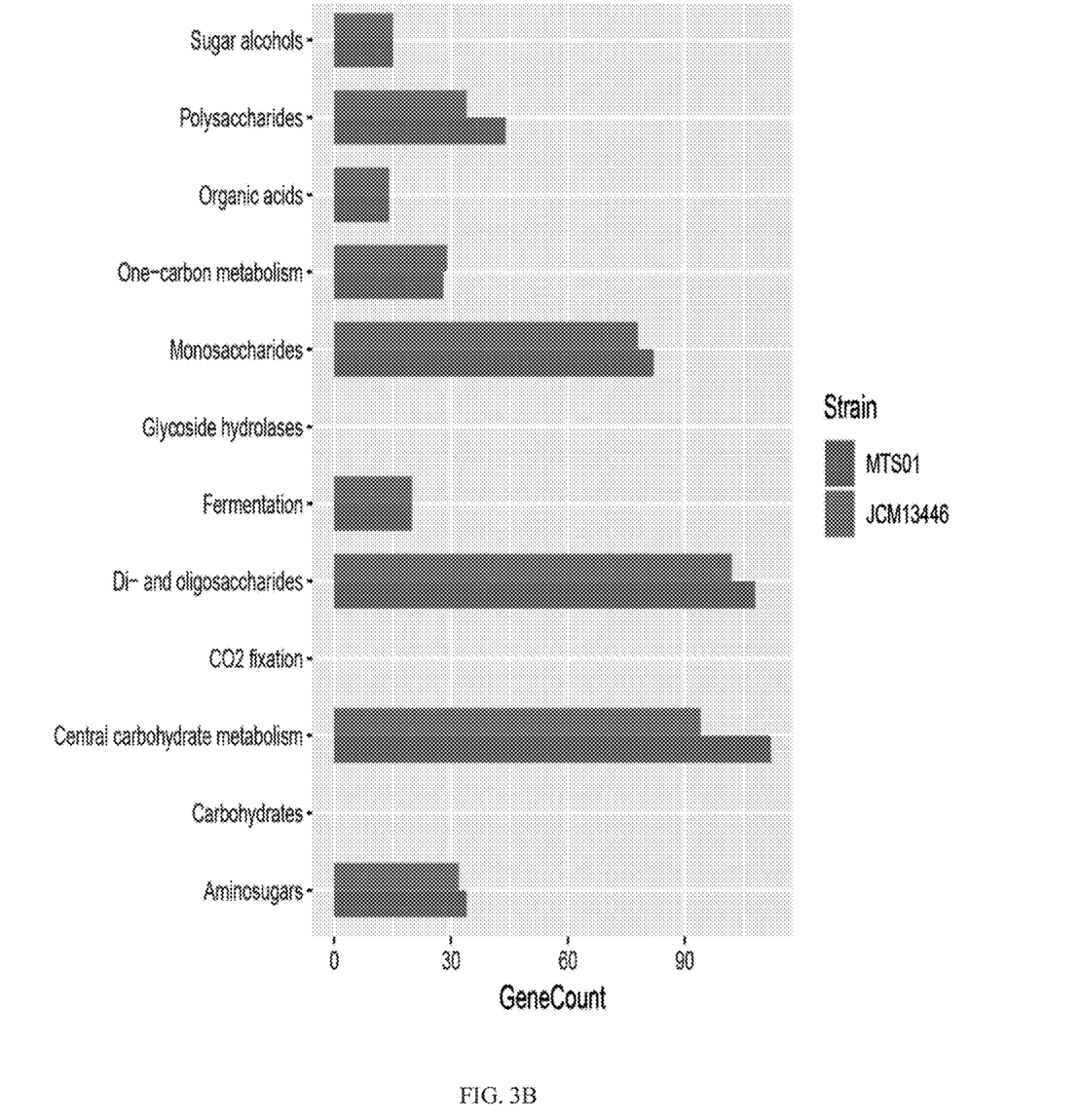
FIG. 3B shows that the functional annotations of the carbohydrate-active enzyme family annotations between the *P. goldsteinii* strain MTS01 and the strain JCM13446.

Based on the above results, the species of the polysaccharide-related gene among the *Parabacteroides goldsteinii* strain MTS01 of the present invention and the strain JCM13446 were further analyzed; wherein, dbCAN2 was used for CAZy (Carbohydrate-active enzyme) family annotations and the results were shown in FIG. 3B; wherein dbCAN2 is a program for automating the annotation of carbohydrate active enzymes, and the CAZy data library records the information of the enzyme family such as degradation, modification, or glycosidic bond production in the structural-related catalytic, carbohydrate-binding modules or functional domains.

The results of the protein annotation comparison of the polysaccharide or carbohydrate associated genes between the *Parabacteroides goldsteinii* strain MTS01 of the present invention and the strain JCM13446 were shown in FIG. 3B. As showing in FIG. 3B, the number of genes associated with polysaccharides, monosaccharides, di-saccharides, oligosaccharides, central carbohydrate metabolism and amino-sugars was all higher in strain MTS01 than in strain JCM13446. The results indicated that the function associated with the polysaccharide was one of the major differences between the *Parabacteroides goldsteinii* strain MTS01 of the present invention and the strain JCM13446.

Figure 4:
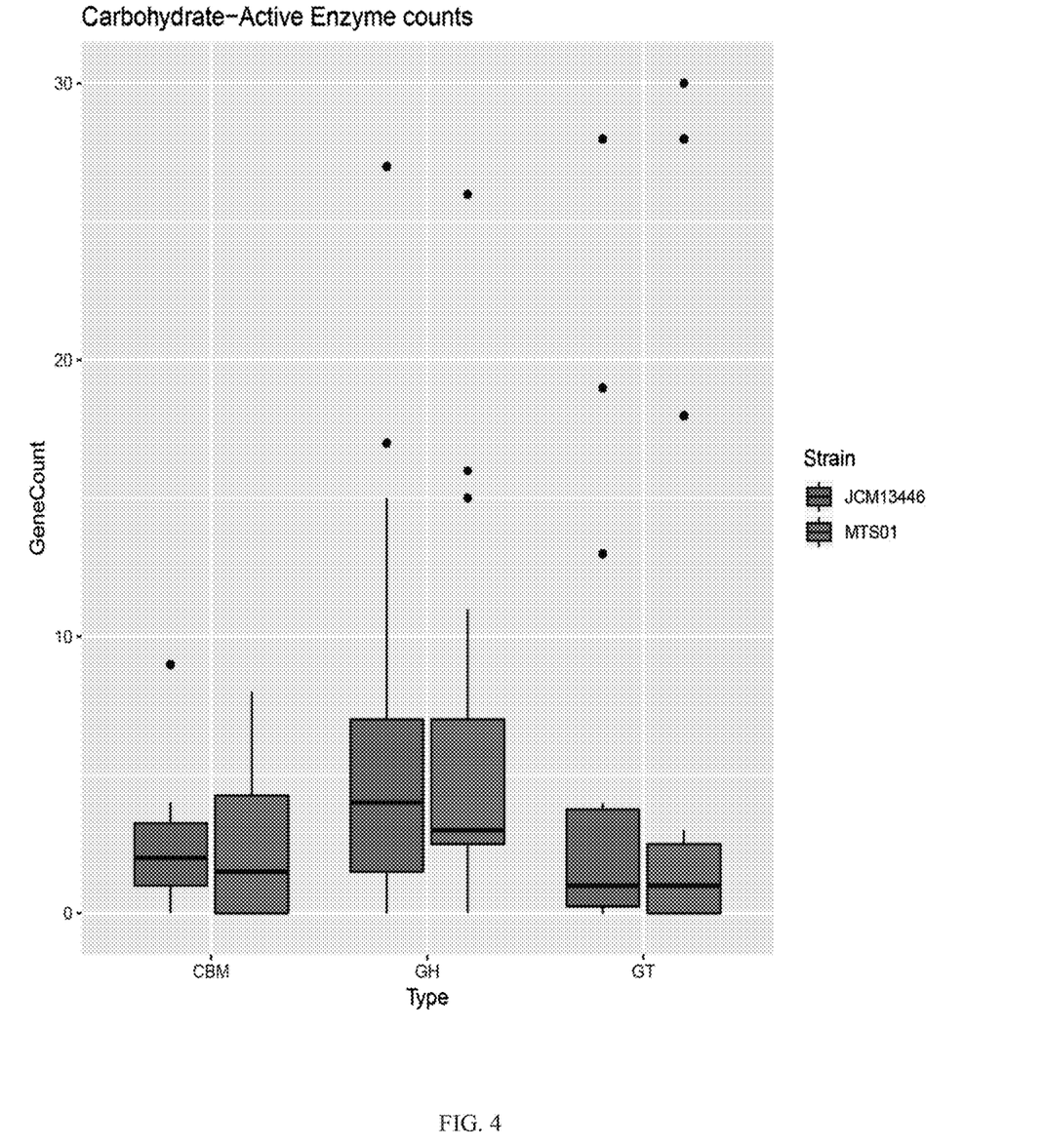
FIG. 4 shows that the comparison of glycosyl hydrolase (GH), glycosyltransferase (GT), and carbohydrate-binding modules (CBM) series between the *P. goldsteinii* strain MTS01 and the strain JCM13446.

Based on the above results, the analysis of the carbohydrate active enzyme annotations obtained through the CAZy data library were further used to generate the box line diagrams of glycosyl hydrolase (GH), glycosyltransferase (GT), and carbohydrate-binding modules (CBM) series of the *Parabacteroides goldsteinii* strain MTS01 of the present invention and the strain JCM13446 by The R Foundation, respectively, and the results were shown in FIG. 4.

The results of the comparison of the carbohydrate active enzyme between the *Parabacteroides goldsteinii* strain MTS01 of the present invention and the strain JCM13446 were shown in FIG. 4. In FIG. 4, the number of glycosyltransferases in the *Parabacteroides goldsteinii* strain MTS01 of the present invention was significantly higher than that in strain JCM13446. The results indicate that the *Parabacteroides goldsteinii* strain MTS01 of the present invention has more abilities on polysaccharides utilization and gains more genes for growth fitness, which enabled the strain MTS01 of the present invention to better adapt to the environment of the individual gastrointestinal tract.

Example 3

Comparison of Aero-Tolerance Between the *Parabacteroides goldsteinii* Strain MTS01 and the Strain JCM13446

*Parabacteroides goldsteinii* is an anaerobic bacterium, thus the embodiment of the present invention was in order to compare the aero-tolerance of the *Parabacteroides goldsteinii* strain MTS01 of the present invention and strain JCM13446. By observing the viability of these two strains in the oxygen supply environment, the environmental tolerance of these two strains was compared. First, the same amount ($1.0\times10^8$ CFU) of the strain MTS01 of the present invention and strain JCM13446 were suspended in normal saline and cultured at 37° C. under an aerobic condition. The viability (i.e., the number of surviving bacteria) of the *Parabacteroides goldsteinii* strain MTS01 of the present invention and strain JCM13446 were determined after 3 hours and 6 hours of culturing, respectively, and the results are shown in FIG. 5.

Figure 5:
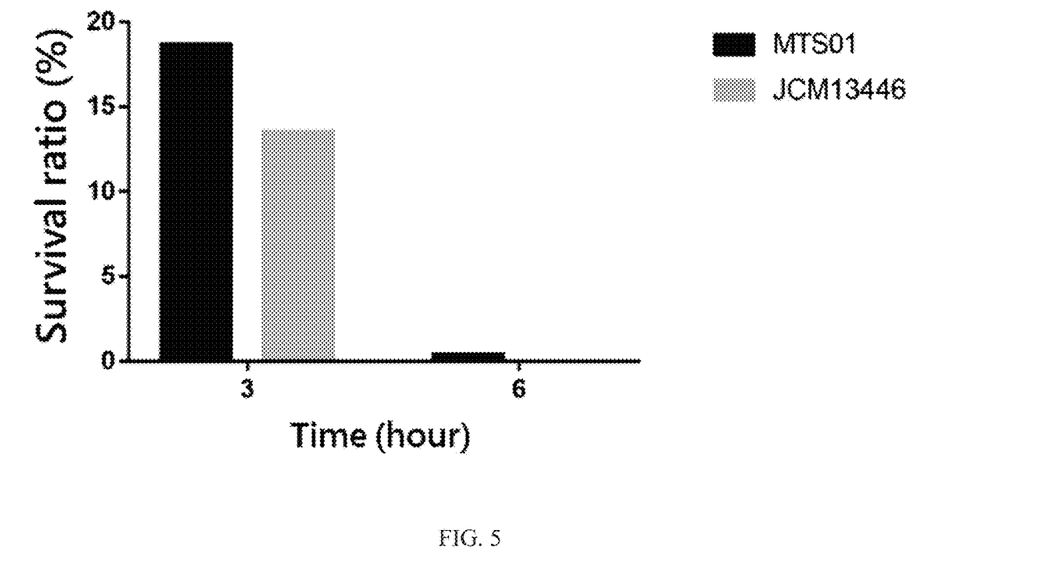
FIG. 5 shows that the comparison of aero-tolerance between the *P. goldsteinii* strain MTS01 and the strain JCM13446.

The comparison of aero-tolerance between the *Parabacteroides goldsteinii* strain MTS01 of the present invention and strain JCM13446 were shown in FIG. 5; wherein the original amount of the cultured bacteria was 100%. As showing in FIG. 5, after the culture was carried out for 3 hours in the oxygen supply environment, the survival rate of the *Parabacteroides goldsteinii* strain MTS01 of the present invention was about 18%, and that of the strain JCM13446 was only 12%; after the culture was carried out for 6 hours in the oxygen supply environment, the survival rate of the *Parabacteroides goldsteinii* strain MTS01 of the present invention could still be detected. On the contrary, the strain JCM13446 was almost dead; that is, the survival rate of the *Parabacteroides goldsteinii* strain MTS01 of the present invention in the oxygen supply environment was significantly higher than that of the strain JCM13446. The results indicated that the *Parabacteroides goldsteinii* strain MTS01 of the present invention had better aero-tolerance and better environmental tolerance than the strain JCM13446, and could be better adapted to different living environments, such as the gastrointestinal tract of individuals.

Example 4

Comparison of Acid-Tolerance Between the *Parabacteroides goldsteinii* Strain MTS01 and the Strain JCM13446

*Parabacteroides goldsteinii* is an enteric bacterium, thus the embodiment of the present invention was in order to compare the acid-tolerance of the *Parabacteroides goldsteinii* strain MTS01 of the present invention and strain JCM13446. By observing the viability of these two strains in a strong acid environment, the environmental tolerance of these two strains was compared. First, the same amount ($1.0\times10^8$ CFU) of the strain MTS01 of the present invention and strain JCM13446 were suspended in a liquid culture medium of *Parabacteroides goldsteinii* described above with a pH of 3, and then cultured at 37° C. under an aerobic condition. The viability (i.e., the number of surviving bacteria) of the *Parabacteroides goldsteinii* strain MTS01 of the present invention and strain JCM13446 were determined after 1 hour and 2 hours of culturing, respectively, and the results are shown in FIG. 6.

Figure 6:
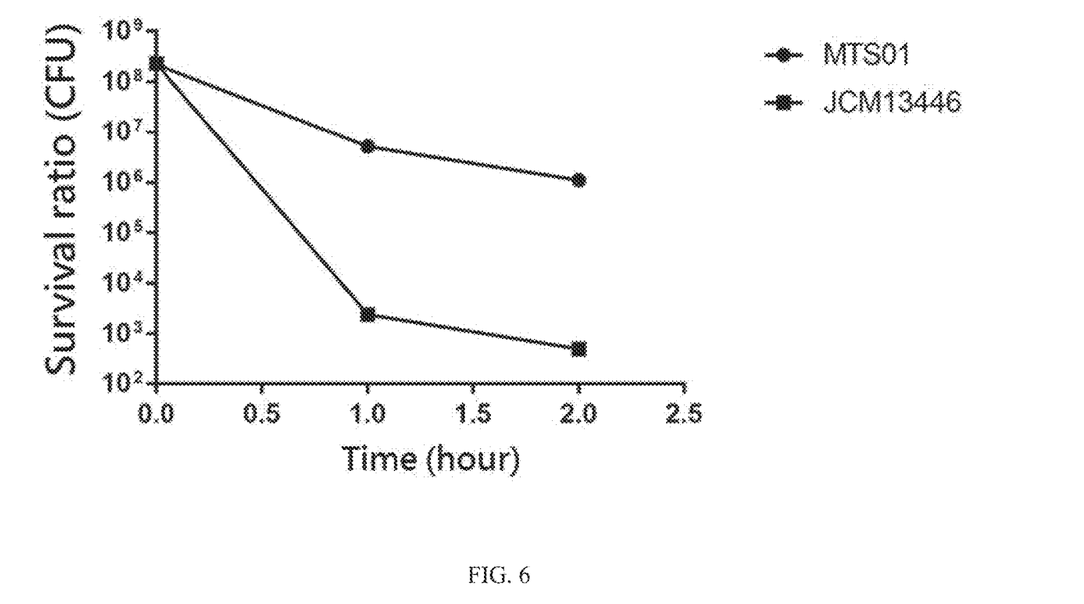
FIG. 6 shows that the comparison of acid-tolerance between the *P. goldsteinii* strain MTS01 and the strain JCM13446.

The comparison of acid-tolerance between the *Parabacteroides goldsteinii* strain MTS01 of the present invention and strain JCM13446 were shown in FIG. 6. As showing in FIG. 6, after the culture was carried out for 1 hour under the condition of pH 3, the number of surviving bacteria of the *Parabacteroides goldsteinii* strain MTS01 of the present invention was still $10^7$ CFU; however, the surviving bacteria of the strain JCM13446 was only 103 CFU; after the culture was carried out for 2 hours under the condition of pH 3, the number of surviving bacteria of the *Parabacteroides goldsteinii* strain MTS01 of the present invention was still maintained in $5\times10^6$ CFU; however, the surviving bacteria of the strain JCM13446 was only $5\times10^2$ CFU, showing that the survival rate of the *Parabacteroides goldsteinii* strain MTS01 of the present invention in an acidic environment was much higher than that of the strain JCM13446. The results indicated that the *Parabacteroides goldsteinii* strain MTS01 of the present invention has better acid-resistance than the strain JCM13446, and could be better adapted to different living environments, especially the gastrointestinal tract of individuals with strong acid environment.

Example 5

Better Anti-Obesity Effect of the *Parabacteroides goldsteinii* Strain MTS1 than the Strain JCM13446

The embodiment of the present invention was in order to compare the anti-obesity effect of the *Parabacteroides goldsteinii* strain MTS01 of the present invention and strain JCM13446. First, the four-week-old C57BL/6Narl male mice were accommodated a period of 1 week, and then the mice were divided into the following four groups (n=5 for each group): (1) the control group of the mice fed with standard chow diet (chow, 13.5% of energy from fat; LabDiet 5001; LabDiet, USA) and were supplemented daily with 100 µL of sterile PBS (vehicle) by intragastric gavage for 8 weeks, (2) the comparison group of the mice fed with high fat diet, HFD, (60% of energy from fat; TestDiet 58Y1; TestDiet, USA) and were supplemented daily with 100 µL of sterile PBS by intragastric gavage for 8 weeks, (3) the experimental group of the mice fed with HFD and were supplemented daily with 100 µL of the *Parabacteroides goldsteinii* strain MTS01 containing $2\times10^9$ CFUs/kg by intragastric gavage for 8 weeks, and (4) the experimental group of the mice fed with HFD and were supplemented daily with 100 µL of the *Parabacteroides goldsteinii* strain JCM13446 containing $2\times10^9$ CFUs/kg by intragastric gavage for 8 weeks.

Figure 7A:
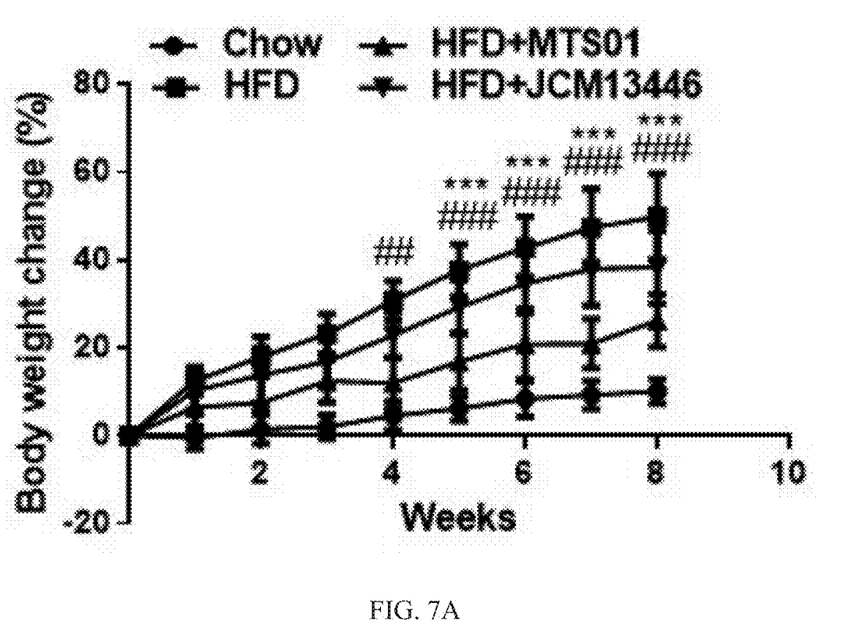
FIG. 7A shows that effects of the *P. goldsteinii* strain MTS01 and the strain JCM13446 on inhibiting the body weight change rate in mice. # represents that the comparison group has a significantly difference compared with the group fed with the strain JCM13446, and * represents that the group fed with the strain JCM13446 has a significant difference compared with the group fed of the strain MTS01 of the present invention; wherein, # or *p<0.05; ## or p<0.01; ### or *p<0.001. Chow represents the mice fed with standard chow diet, and HFD represents the mice fed with high fat diet.
Figure 7B:
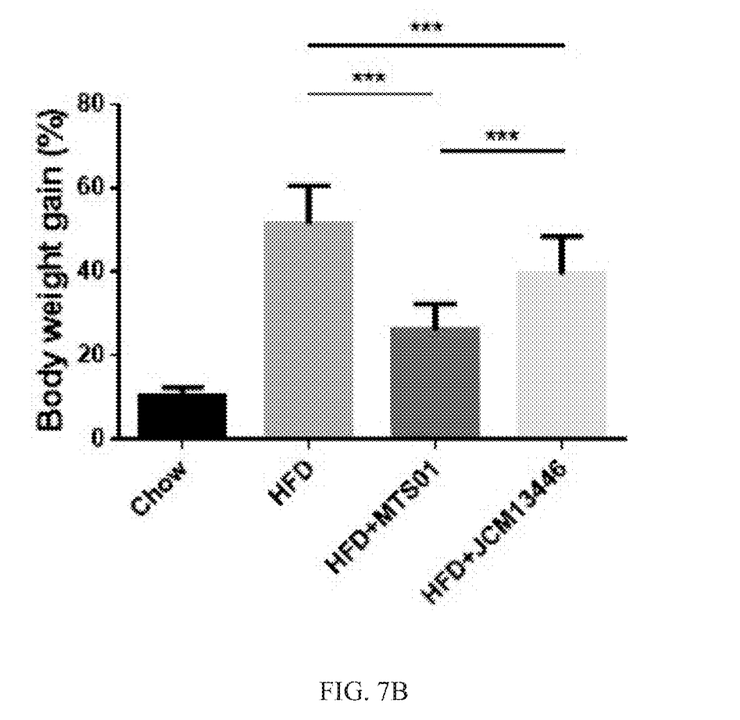
FIG. 7B shows that effects of the *P. goldsteinii* strain MTS01 and the strain JCM13446 on inhibiting the value of the body weight gain in mice. ***p<0.001.

Next, the body weight of each group of mice was monitored weekly for 8 weeks, and the final body weight at week 8 subtracted from the starting weight at week 0 as the value of the body weight gain of each group of mice and the value was expressed as a percentage, and the result was shown in FIG. 7B. The value of body weight gain was divided by the starting body weight and expressed as a percentage to calculate the body weight change rate of each group of mice, and the results were shown in FIG. 7A. After 8 weeks, each group of mice was sacrificed, and the subcutaneous fat was weighed to calculate the value of the subcutaneous fat mass gain of each group of mice, and the results were shown in FIG. 7C; the visceral adipose tissues (i.e. epididymal white adipose tissues) was also weighed to calculate the value of the epididymal fat mass gain of each group of mice, and the results were shown in FIG. 7D. The data of the experimental results were shown as mean t standard deviation, and all statistical analyses were performed by standard one-way ANOVA with Dunnett's multiple comparison test. (# represents that the comparison group has a significantly difference compared with the group fed with the strain JCM13446, and * represents that the group fed with the strain JCM13446 has a significant difference compared with the group fed of the strain MTS01 of the present invention; wherein, # or *p<0.05; ## or p<0.01; ### or *p<0.001.)

The effects of the *Parabacteroides goldsteinii* strain MTS01 of the present invention and the strain JCM13446 on inhibiting the body weight change rate in mice were shown in FIG. 7A; and the effects of the *Parabacteroides goldsteinii* strain MTS01 of the present invention and the strain JCM13446 on inhibiting the value of the body weight gain in mice were shown in FIG. 7B. As showing in FIG. 7A and FIG. 7B, after being fed for 4 to 8 weeks, the body weight change rate of the mice in the comparison group fed with the high-fat diet alone was significantly higher than that of the mice fed with the MTS01 strain of the present invention or the JCM13446 strain. Besides, after being fed for 8 weeks, the value of the body weight gain of the mice in the comparison group fed with the high-fat diet alone was also significantly higher than that of the mice fed with these two strains of the *Parabacteroides goldsteinii*. These results indicated that both of the *Parabacteroides goldsteinii* strain MTS01 of the present invention or the strain JCM13446 could effectively inhibit the body weight gain of an individual; however, after being fed the high-fat diet for 5 to 8 weeks, the mice fed with the *Parabacteroides goldsteinii* strain MTS01 of the present invention had a significantly lower body weight change rate than the mice fed with the strain JCM13446, and after being fed the high-fat diet for 8 weeks, the mice fed with the *Parabacteroides goldsteinii* strain MTS01 of the present invention had a significantly lower value of the body weight gain than the mice fed with the strain JCM13446. The results indicated that the *Parabacteroides goldsteinii* strain MTS01 of the present invention could more effective inhibit the body weight gain of the individual than the strain JCM13446.

Figure 7C:
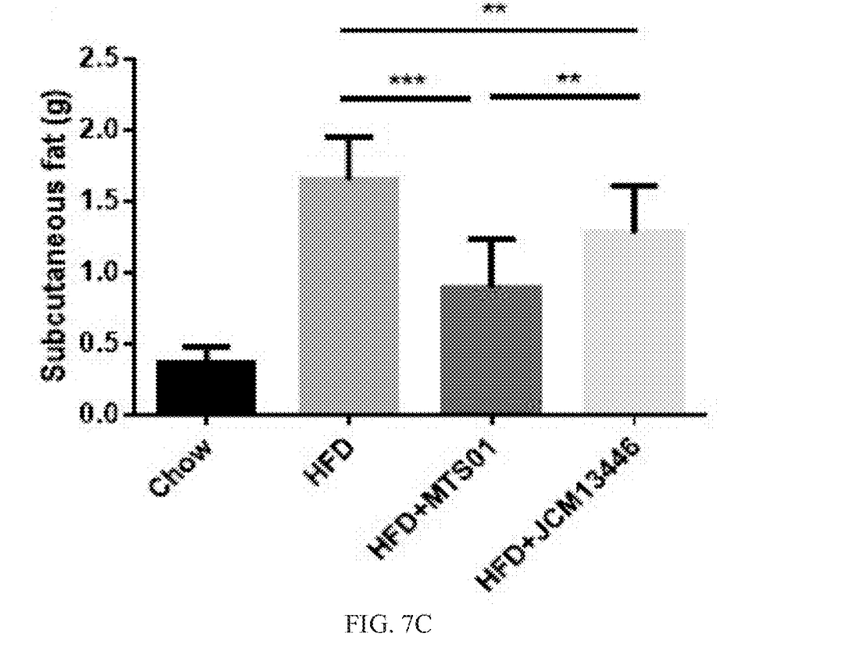
FIG. 7C shows that effects of the *P. goldsteinii* strain MTS01 and the strain JCM13446 on inhibiting the value of the subcutaneous fat mass gain in mice. p<0.01; *p<0.001.

The effects of the *Parabacteroides goldsteinii* strain MTS01 of the present invention and the strain JCM13446 on inhibiting the value of the subcutaneous fat mass gain in mice were shown in FIG. 7C. As showing in FIG. 7C, after being fed for 8 weeks, the value of the subcutaneous fat mass gain of the mice in the comparison group fed with the high-fat diet alone was also significantly higher than that of the mice fed with the *Parabacteroides goldsteinii* strain MTS01 and the strain JCM13446. These results indicated that both of the *Parabacteroides goldsteinii* strain MTS01 of the present invention or the strain JCM13446 could effectively inhibit the subcutaneous fat mass gain of an individual; however, after being fed the high-fat diet for 8 weeks, the mice fed with the *Parabacteroides goldsteinii* strain MTS01 of the present invention had a significantly lower value of the subcutaneous fat mass gain than the mice fed with the strain JCM13446. The results indicated that the *Parabacteroides goldsteinii* strain MTS01 of the present invention was more effective in inhibiting the subcutaneous fat mass gain of the individual than the strain JCM13446.

Figure 7D:
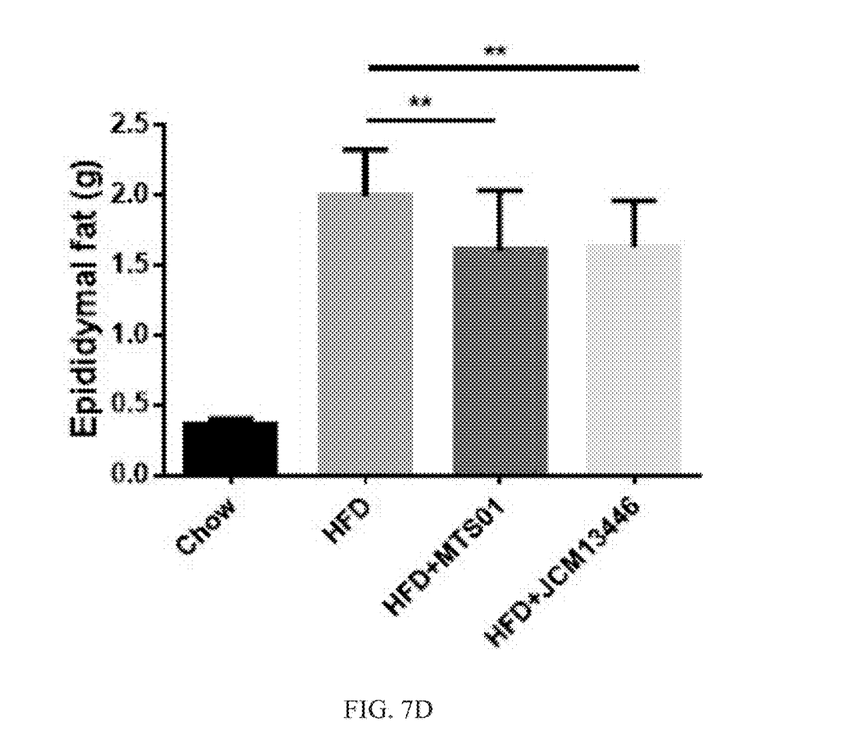
FIG. 7D shows that effects of the *P. goldsteinii* strain MTS01 and the strain JCM13446 on inhibiting the value of the epididymal fat mass gain in mice. **p<0.01.

The effects of the *Parabacteroides goldsteinii* strain MTS01 of the present invention and the strain JCM13446 on inhibiting the value of the epididymal fat mass gain in mice were shown in FIG. 7D. As showing in FIG. 7D, after being fed for 8 weeks, the value of the epididymal fat mass gain of the mice in the comparison group fed with the high-fat diet alone was also significantly higher than that of the mice fed with the *Parabacteroides goldsteinii* strain MTS01 and the strain JCM13446. These results indicated that both of the *Parabacteroides goldsteinii* strain MTS01 of the present invention or the strain JCM13446 could effectively inhibit the epididymal fat mass gain of an individual; in addition, after being fed the high-fat diet for 8 weeks, the mice fed with the *Parabacteroides goldsteinii* strain MTS01 of the present invention had a similar value of the epididymal fat mass gain with the mice fed with the strain JCM13446.

The above results indicated that the *Parabacteroides goldsteinii* strain MTS01 of the present invention could more significantly inhibit the body weight gain, more effectively reduce the body weight change rate, and more effectively inhibit the subcutaneous fat mass gain of individuals fed with a high-fat diet compared with the strain JCM13446. The results indicated that the *Parabacteroides goldsteinii* strain MTS01 of the present invention had better effect on preventing the obesity and could more effectively inhibit the obesity of individuals than the strain JCM13446, and achieve the effect of inhibiting obesity.

Example 6

Effect of the *Parabacteroides goldsteinii* Strain MTS01 on Inhibiting the Increase of the Body Weight of Obese Individuals The embodiment of the present invention was in order to investigate the effect of the *Parabacteroides goldsteinii* strain MTS01 on inhibiting the increase of the body weight of obese individuals. First, the four-week-old C57BL/6Narl male mice were accommodated a period of 1 week, and then the mice were divided into the following three groups (n=5 for each group): (1) the control group of the mice fed with standard chow diet for 6 weeks and then were supplemented daily with 100 μL of sterile PBS by intragastric gavage for next 10 weeks, (2) the comparison group of the mice fed with HFD for 6 weeks and then were supplemented daily with 100 μL of sterile PBS by intragastric gavage for next 10 weeks, and (3) the experimental group of mice fed with HFD for 6 weeks and then were supplemented daily with 100 μL of the *Parabacteroides goldsteinii* strain MTS01 containing $2 \times 10^9$ CFUs/kg by intragastric gavage for next 10 weeks.

Figure 8A:
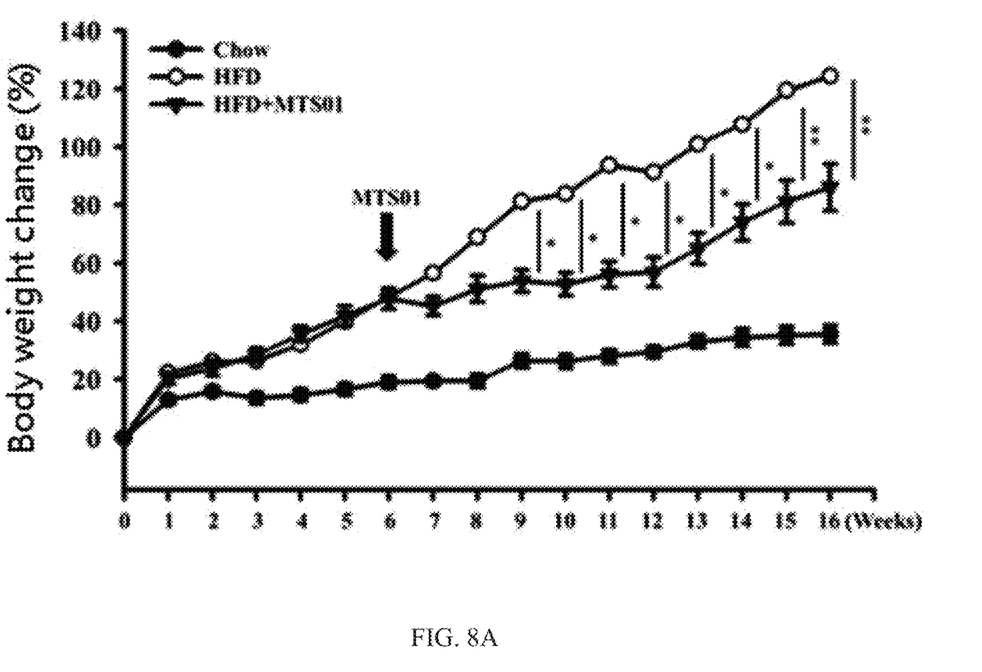
FIG. 8A shows that effects of the *P. goldsteinii* strain MTS01 on inhibiting the body weight change rate in obese individuals. *p<0.05; **p<0.01.
Figure 8B:
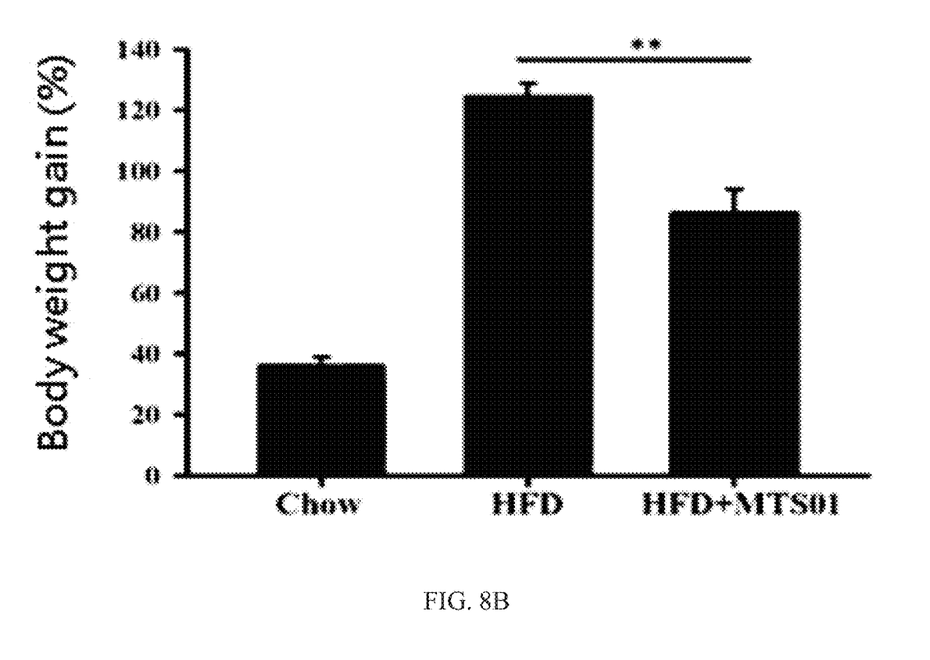
FIG. 8B shows that effects of the *P. goldsteinii* strain MTS01 on inhibiting the value of the body weight gain in obese individuals. **p<0.01.

The body weight of each group of mice was monitored weekly for 16 weeks, and the final body weight at week 16 subtracted from the starting weight at week 0 as the value of the body weight gain of each group of mice and the value was expressed as a percentage, and the result was shown in FIG. 8B. The value of body weight gain was divided by the starting body weight and expressed as a percentage to calculate the body weight change rate of each group of mice, and the results were shown in FIG. 8A. The data of the experimental results were shown as mean t standard deviation, and all statistical analyses were performed by standard one-way ANOVA with Dunnett's multiple comparison test. (*p<0.05; p<0.01; *p<0.001.)

The effects of the *Parabacteroides goldsteinii* strain MTS01 of the present invention on inhibiting the body weight change rate in obese mice were shown in FIG. 8A; and the effects of the *Parabacteroides goldsteinii* strain MTS01 of the present invention on inhibiting the value of the body weight gain in obese mice were shown in FIG. 8B. As showing in FIG. 8A and FIG. 8B, after being fed with the high-fat diet for 6 weeks, the body weight of the mice indeed increased to establish an animal model of obesity, and after starting to feed the *Parabacteroides goldsteinii* strain MTS01 of the present invention for 3 weeks, the value of body weight gain of the obese mice was significantly slowed down. After continuously fed the *Parabacteroides goldsteinii* strain MTS01 of the present invention for about 10 weeks, the value of the body weight gain of the obese mice was significantly inhibited about 40%. The results indicated that the *Parabacteroides goldsteinii* strain MTS01 of the present invention could not only effectively prevent the obesity of an individual, but also effectively slow down the body weight gain of an obese individual to achieve the effect of treating obesity.

The use of the *Parabacteroides goldsteinii* strain MTS01 of the present invention in the prevention or treatment of obesity can be, but is not limited to, oral administration to the subject in need thereof. The composition can be orally administered along with food; therefore, the preparation of the composition comprising the *Parabacteroides goldsteinii* strain MTS01 of the present invention can further include a protein, a monosaccharide, a disaccharide, an oligosaccharide, an oligosaccharide, a polysaccharide, a carbohydrate, an amino acid, a lipid, a vitamin, or any combination well-known in the art.

Otherwise, the preparation of the composition comprising the *Parabacteroides goldsteinii* strain MTS01 of the present invention can further include a pharmaceutically acceptable excipient, carrier, adjuvant, or food additive. The composition is in the form of, but is not limited to, a spray, a solution, a semi-solid state, a solid state, a gelatin capsule, a soft capsule, a tablet, an oral strip, a chewing gum or a freeze-dried powder preparation in order to transfer the *Parabacteroides goldsteinii* strain MTS01 of the present invention to the intestinal tract or to partially or fully colonize the intestinal tract. Simultaneously, the *Parabacteroides goldsteinii* strain MTS01 of the present invention or the composition containing other ingredients can be further used in the preparation of a food, a health food, or a dietary supplement.

In summary, the results of the whole-genome analysis indicate that there are 5,498 predicted protein-coding genes in the novel *Parabacteroides goldsteinii* strain MTS01 isolated from the feces of C57BL/6 mice. Wherein, compared with the *Parabacteroides goldsteinii* strain JCM13446, which is a clinical isolate cultured from abdominal fluid of human intestinal origin, the 586 genes of these 5,498 genes of the strain MTS01 are only 70% or less identical to the strains JCM13446, and the 610 genes of the *Parabacteroides goldsteinii* strain MTS01 of the present invention are not present in the strain JCM13446, indicating that the *Parabacteroides goldsteinii* strain MTS01 of the present invention and the strain JCM13446 have a high degree of genomic variability, and the 610 unique genes in the strain MTS01 of the present invention may be obtained from other commensal bacteria through bacterium-bacterium genetic determinants transfer machinery.

Moreover, the results of the protein annotation analysis indicate that the number of genes encoding phages, prophages, transposable elements, and plasmids of the strain MTS01 is significantly higher than that of the strain JCM13446. Based on the results, the species of the polysaccharide-related gene among the *Parabacteroides goldsteinii* strain MTS01 of the present invention and the strain JCM13446 are further analyzed, and the results show that the number of genes associated with polysaccharides, monosaccharides, di-saccharides, oligo-saccharides, central carbohydrate metabolism and amino-sugars is all higher in strain MTS01 than in strain JCM13446, and the number of glycosyltransferases in the *Parabacteroides goldsteinii* strain MTS01 of the present invention is significantly higher than that in strain JCM13446. The results indicate that the *Parabacteroides goldsteinii* strain MTS01 of the present invention has more abilities on polysaccharides utilization and gains more genes for growth fitness, which enables the strain MTS01 of the present invention to better adapt to the environment of the individual gastrointestinal tract.

The environmental tolerance of these two strains is further performed, and the results show that the *Parabacteroides goldsteinii* strain MTS01 of the present invention has better aero-tolerance and better acid-resistance than the strain JCM13446, and can be better adapted to different living environments, especially the gastrointestinal tract of individuals with strong acid environment.

Finally, results of the effect on preventing obesity indicate that the *Parabacteroides goldsteinii* strain MTS01 of the present invention can more significantly inhibit the body weight gain of individuals fed a high-fat diet and more effectively reduce the body weight change rate compared to the strain JCM13446, and the *Parabacteroides goldsteinii* strain MTS01 of the present invention can also significantly inhibit the subcutaneous fat mass gain of individuals fed the high-fat diet, indicating that the *Parabacteroides goldsteinii* strain MTS01 of the present invention has better effect on preventing the obesity and can more effectively inhibit the obesity of individuals than the strain JCM13446, and achieve the effect of inhibiting obesity. At the same time, the results of the effect on inhibiting the body weight gain of obese individuals indicate that the *Parabacteroides goldsteinii* strain MTS01 of the present invention can not only effectively prevent the obesity of an individual, but also effectively slow down the body weight gain of an obese individual to achieve the effect of treating obesity.

The present invention provides a novel *Parabacteroides goldsteinii* strain MTS01 for the preparation of a pharmaceutical composition for preventing or treating obesity; wherein the *Parabacteroides goldsteinii* strain MTS01 of the present invention is derived from the gastrointestinal tract and is a probiotic strain which can well adapt to the gastrointestinal environment that can enhance the benefits of the probiotic strain in practical application, and the probiotic strain of the present invention is more effective in preventing and treating obesity; therefore, the *Parabacteroides goldsteinii* strain MTS01 of the present invention can be effectively applied to the prevention or treatment of obesity and the preparation of related pharmaceutical compositions.

What is claimed is:

1. A method of preventing or treating obesity, comprising administering to a subject in need thereof a composition comprising an effective amount of a *Parabacteroides goldsteinii* MTS01 (deposited at Leibniz Institute DSMZ, deposit number DSM 32939).

2. The method according to claim 1, wherein the *Parabacteroides goldsteinii* DSM 32939 enhances environmental tolerance.

3. The method according to claim 2, wherein the environmental tolerance is aero-tolerance or acid-tolerance.

4. The method according to claim 1, wherein the *Parabacteroides goldsteinii* DSM 32939 is a live bacterium.

5. The method according to claim 1, wherein the effective amount of the *Parabacteroides goldsteinii* MTS01 (deposited at Leibniz Institute DSMZ, deposit number DSM 32939) is at least $2 \times 10^9$ CFUs/kg of body weight per day.

6. The method according to claim 1, wherein the composition inhibits the body weight gain of the subject.

7. The method according to claim 6, wherein the subject is a non-obese subject or an obese subject.

8. The method according to claim 1, wherein the composition further comprises a metabolite of the *Parabacteroides goldsteinii* MTS01 (deposited at Leibniz Institute DSMZ, deposit number DSM 32939).

9. The method according to claim 8, wherein the composition inhibits the body weight gain of the subject.

10. The method according to claim 9, wherein the subject is a non-obese subject or an obese subject.

11. The method according to claim 1, wherein the composition further comprises other bacteria.

12. The method according to claim 1, wherein the composition further comprises a pharmaceutically acceptable excipient, carrier, adjuvant, or food additive.

13. The method according to claim 1, wherein the composition is in the form of a spray, a solution, a semi-solid state, a solid state, a gelatin capsule, a soft capsule, a tablet, an oral strip, a chewing gum, or a freeze-dried powder preparation.

* * * * *